(12) United States Patent
Galic

(10) Patent No.: US 8,278,289 B2
(45) Date of Patent: Oct. 2, 2012

(54) BOROXINE COMPOSITION FOR REMOVAL OF SKIN CHANGES

(76) Inventor: Borivoj Galic, Sarajevo (BA)

( * ) Notice: Subject to any disclaimer, the term of this patent is extended or adjusted under 35 U.S.C. 154(b) by 45 days.

(21) Appl. No.: 12/294,017

(22) PCT Filed: Mar. 21, 2006

(86) PCT No.: PCT/IB2006/002033
§ 371 (c)(1),
(2), (4) Date: Mar. 2, 2009

(87) PCT Pub. No.: WO2007/107809
PCT Pub. Date: Sep. 27, 2007

(65) Prior Publication Data
US 2009/0238897 A1    Sep. 24, 2009

(51) Int. Cl.
*A61K 31/69*    (2006.01)
(52) U.S. Cl. .......... 514/64; 424/660; 424/657; 424/600; 423/277; 423/276
(58) Field of Classification Search .................. None
See application file for complete search history.

(56) References Cited

U.S. PATENT DOCUMENTS

| | | | | |
|---|---|---|---|---|
| 3,103,532 | A * | 9/1963 | Dykstra | 546/13 |
| 4,110,426 | A * | 8/1978 | Barnhurst et al. | 424/46 |
| 7,507,842 | B2 | 3/2009 | Bednarski et al. | |
| 2002/0016271 | A1* | 2/2002 | Racherla | 510/141 |
| 2003/0109751 | A1* | 6/2003 | Schubert | 564/8 |

OTHER PUBLICATIONS

"Dermatological Pharmacology" by Guzzo et al. in Goodman & Gilman's The Pharmacological Basis of Therapeutics, 9th Ed., Hardman et al., Eds., McGraw-Hill (New York), pp. 1593-1616 (1996).*
"The Chemistry of Fluorine and its Inorganic Compounds," by I. G. Ryss, State Publishing House for Scientific, Technical and Chemical Literature, Moscow 1956 (English Translation U.S. Atomic Energy Commission Translation Series AEC-tr-3927), pp. 558-560.*
"Infrared absorption spectra of the hydroxyfluoroborate complexes of potassium and sodium," by Akhmanova et al., Optika i Spektroskopiya 8, 498-504, 498 (1960).*
"Cancer Drug Design and Discovery" by Neidle (Ed.), Elsevier/Academic Press, pp. 427-431 (2008).*
Database CA, Chemical Abstracts Service; Columbus, Ohio, US; Egorov V.A. et al. "X-ray diffraction study of potassium tetrafluorotriborate $K_2[B_3O_3F_4OH]$"; XP002414019, (May 12, 1984).
Database CA, Chemical Abstracts Service; Columbus, Ohio, US; Bastanova, L.R. et al. "Interaction of boric acid with potassium and ammonium fluorides"; XP002414020, (May 12, 1934).
Database CA, Chemical Abstracts Service; Columbus, Ohio, US; Akhmanova, M.V. et al. "Investigation of stability of hydroxyfluoroboric complexes of potassium and sodium in their aqueous solutions by infrared absorption spectra"; XP002414021, (Apr. 22, 2001).
Database CA, Chemical Abstracts Service; Columbus, Ohio, US; AKhmanova, M.V. et al. "Study of the state of ions in aqueous solutions of potassium and sodium fluoroborate-containing compounds by the infrared spectrum method"; XP002414022, (1962).

* cited by examiner

*Primary Examiner* — Anish Gupta
*Assistant Examiner* — Theodore R West
(74) *Attorney, Agent, or Firm* — Knobbe Martens Olson & Bear LLP

(57) ABSTRACT

The present invention relates to the field of skin disorders, particularly to the prevention and/or treatment of benignant or malignant changes of the epidermis visible in form of e.g. nevus. A pharmaceutical, dermatological and/or cosmetic composition is disclosed comprising as active constituent the boroxine compound. The present invention further provides the respective uses of the boroxine compound in medicine, particularly in the field of skin disorders, and in dermatological and/or cosmetic applications.

4 Claims, No Drawings

BOROXINE COMPOSITION FOR REMOVAL OF SKIN CHANGES

This application is U.S. National Phase of International Application PCT/IB2006/002033, filed Mar. 21, 2006 designating the U.S., and published in English as WO 2007/107809 on Sep. 27, 2007.

The present invention relates to the field of skin disorders, particularly to the prevention and/or treatment of benignant or malignant changes of the epidermis which are visible in form of e.g. black nevus. A pharmaceutical, dermatological and/or cosmetic composition is disclosed comprising as active constituent a boroxine structured borate compound. The present invention further provides the respective uses of said compound in medicine, particularly in the field of skin disorders, and in dermatological and/or cosmetic applications.

There exist various kinds of benignant or malignant changes of the skin, which have to be removed either due to medical reasons or for cosmetically purposes. Around 0.37% of the European population suffers from malignant skin disorders or skin cancers, which are usually divided in melanomas, developing from melanocytes, and non-melanomas, originating from other skin cells.

The human skin has three layers, epidermis, dermis and subcutis. The epidermis as top layer of the skin is very thin and serves to protect the deeper layers and the internal organs. The epidermis itself has three layers: the upper, middle and bottom layer composed of basal cells, which divide to form keratinocytes (or squamous cells). Melanocytes are also present in the epidermis and produce the pigment melanin giving the skin a tan or brown color. A basement membrane comprised of extra-cellular matrix separates the epidermis from the deeper layers of skin.

Of particular importance is the protective function of melanin pigmentation since its absorptive capacity can considerably weaken harmful energy-rich UV radiation from sun. UV irradiation induces the formation of melanin in special sections of the melanocytes, the melanosomes. The melanin formed is transported into the keratinocytes, where it becomes visible as a brown skin color. Depending on higher amounts of melanin produced, skin color deepens. Uneven distribution of the melanocytes in sections of skin tissue leads to the undesired appearance of differing skin tones and local irregular hyperpigmentations, which manifest themselves, for example, in the form of pregnancy-related marks, age spots, freckles or other pigment disorders. Such benignant changes of skin may mutate, depending e.g. on environmental influences, to malignant skin disorders or skin cancers.

The most harmful skin cancer is melanoma originating in cells of the melanocytic system of the skin. Metastasis of melanoma is common. Although melanoma accounts for only about 4% of all skin cancer cases, it causes most skin cancer-related deaths. Melanomas usually appear as black or dark brown moles having often an irregular shape.

The conventional treatment of cutaneous melanoma has been excision with a deep and wide margin of normal appearing tissue surrounding the tumour depending on the depth and thickness of the cancerous mole. However, microscopic satellite sites potentially occurring in the otherwise normal appearing skin surrounding the melanoma may be disturbed, and host resistance may be reduced following the excision of the melanoma. A decrease in host resistance may result in the appearance of cancer in distant sites of the body (metastases). Although it is common to excise a margin of tissue surrounding the tumour, it is well known that increasing the size of the surgical margin to greater and greater extent does not affect survival rate.

Cancers of the skin developing from cells different from melanocytes are called non-melanomas (usually basal cell and squamous cell cancers) representing the most common cancers of the skin. They rarely spread to sites elsewhere in the body and are therefore considered less dangerous. Non-melanoma skin cancers are among the most common of malignant diseases accounting for one-third of all cancers. There are approximately three million cases of NMSC reported annually in North America, Europe, Japan, Australia and South Africa.

Basal Cell Carcinomas (BCC) account for 75-80% of all non-melanoma skin cancers. BCC arises from the basal cells of the epidermis and its appendages. It is characterised by slow local growth, which is capable of causing extensive tissue damage resulting in loss of organ function and disfigurement. The most common etiological factor in BCC is exposure to ultraviolet light (UV). Consequently, areas of skin with high levels of UV exposure, such as the head or neck, are most commonly affected. Although metastases are rare these neoplasms may have fatal consequences if left untreated. A number of factors lead to the development of multiple basal cell carcinoma (MBCC) including conditions such as nevoid basal cell carcinoma syndrome (NBCCS, basal cell nevoid syndrome (BCNS) or Gorlin-Goltz syndrome), xeroderma pigmentosum and immunosuppression due to intensive immuno-suppressive therapy administered after organ transplant, or radiation exposure at a young age particularly for the treatment of acne.

Squamous Cell Carcinomas (SCC) represent the remaining 20-25% of NMSC and are: usually fast-growing and prone to metastasize if remain untreated. SCC also tends to affect areas of skin with high levels of UV exposure and is occurs preliminary in persons who have undergone an immunosuppressive therapy. There is evidence that actinic keratosis (AK) is a first warning sign in the development of SCC. Without treatment, some patients with AK are prone to develop one or more lesions that invade the dermis as squamous cell carcinoma.

Current therapies for NMSC include surgical excision, cryosurgery, electrodessication and curettage (ED&C), radiation, and carbon dioxide laser treatment. The cure rates vary according to the therapy, tumour size, and anatomic location but are generally quite high for primary tumours and slightly less for recurrent tumours. However, the current therapies can be time consuming especially where multiple tumours must be treated. Also, the efficacy is highly dependent on the skill of the surgeon and their adherence to the surgical protocol. In addition, there is the possibility of adverse cosmetic effects such as scarring or hyperpigmentation. The necessity of treating multiple tumours, such as in MBCC, increases the likelihood of the patient experiencing unacceptable disfigurement or scarring. Tumours on the head, face, or neck present a particular challenge since any disfigurement is likely to have a profound psychological effect. Therefore, treatments for NMSC should be efficacious while having a regard for the appearance of the patient. Such kind of treatment is e.g. disclosed in EP0815797 relating to a laser treating apparatus allowing irradiation and removal of nevus on skin.

Alternative methods include both medical treatment and surgical steps. In CN1647798 a bleaching composition for the removal of black nevus is disclosed. The composition comprises hydrogen peroxide, water oxydone, dexamethasone, lidocaine and adnephrine. The respective process to eliminate black nevus includes: cleaning of the skin surface to be treated; pricking black nevus with three-edged needle or disposable syringe until effusion of blood; squeezing black nevus and eliminating effusion; and dipping the composition onto gauze and dressing the gauze to the affected part for 30-60 min. The process is repeated once every week until eliminating black nevus.

Apart from the above mentioned malignant skin disorders; there also exist numerous benignant changes of the skin. There may exist medical indications to remove such changes, if the patient has a (genetic) tendency to develop either skin cancers or other cancers, or also cosmetic reasons in case of an undesired irregular hyperpigmentation.

Particularly, in the countries of the western hemisphere there is an increased interest in effectively balancing the appearance of irregularly pigmented sections of skin, which is often age-related, such as, for example, pregnancy-related marks or age spots.

There has hitherto been no lack of attempts to correct pigment disorders, and in the past, a large number of different substances have already been proposed which intervene in various regulation mechanisms of pigment formation.

A targeted effect can be induced on skin tones and disorders by either breaking down the melanin present, or achieving a reduction in melanin formation.

For example, use was made previously of, inter alia, mercury and bismuth salts which irreversibly inhibit tyrosinase. However, due to the high toxicity of mercury and bismuth salts, such substances are no longer used in cosmetic compositions. The use of cell-toxic compounds, such as, for example, hydroquinone and derivatives thereof, which bring about direct destruction of the melanocytes and can only be applied to small areas of skin due to their harmful effect on the skin, is no longer approved in most countries either.

Most standard commercial skin-lightening compositions therefore usually comprise tyrosinase inhibitors of greater or lesser effectiveness. A number of substances have these properties. The palette of materials used therefore includes, in addition to highly diverse plant extracts, vitamin C and ascorbic acid derivatives, and also heterocyclic compounds, such as, for example, pyranone derivatives.

An external applicable composition for removing pigmented nevus of skin, verruca and neoplasm is disclosed in CN 1321466. The composition comprises calcium oxide, sodium bicarbonate, sodium salicylate, procaine, prednisolone acetate and ethyl alcohol.

Respective compositions directed solely to an improved appearance of respective skin parts without any surgical step are e.g. disclosed in CN1240653, wherein a wart removing pill or capsule for mainly treating flat nevus, ordinary wart, sagittal wart and virus soft wart. It is prepared from substances such as arnebia root, sunflower, redpeony root, liquorice root, isatis root, etc through crushing.

In U.S. Pat. No. 5,538,740 an active ingredient used for inter alia preventing skin cancer and in cosmetic compositions is obtained from live gastropoda (such as snails), which are physically stimulated to secrete a fluid comprising the active substance.

An external applicable skin preparation for preventing and reducing effects on pigmentation in skin such as blackening, dermal stains or ephelides of the skin after sunburn is disclosed in JP10001438. Suitable dosage forms are creams, lotions or oils.

The above-mentioned methods directed to the removal of malignant changes of the skin rely preliminary on the application of surgical steps, which exhibit several drawbacks, since surgical steps have to be performed on the one hand by medical personal and are on the other hand accompanied by e.g. an increased risk of infection and a possible formation of scars.

The regimen according to the art did not, so far, provide a sufficient treatment of malignant/benignant of changes of the skin. There still exists a need in finding alternative solutions allowing the treatment of both malignant and/or benignant changes of the skin avoiding surgical steps and the respective accompanying drawbacks. Such a solution should preferably comprise an active ingredient bringing about a significant effect even in low use concentrations. Moreover, such an active ingredient should be non-toxic, very well tolerated by the skin, have a high compatibility with other ingredients and be able to be incorporated into skin-treatment compositions without problems. It is particularly desirable if this active ingredient may be additionally prepared in a simple and cost-effective manner and be produced in a form which can be purified easily and thus satisfies the high purity requirements placed on cosmetics and dermatological active ingredients.

It is therefore an object of the present invention to provide such an active ingredient which has the ability, in either pharmaceutical, cosmetic and dermatological formulations, to remove both malignant/benignant changes of the skin and/or to effectively even up the appearance of irregularly pigmented areas of skin, such as, for example, pregnancy-related marks or age spots.

This objective has been achieved by a borate compound in a boroxine structure having the following general formula:

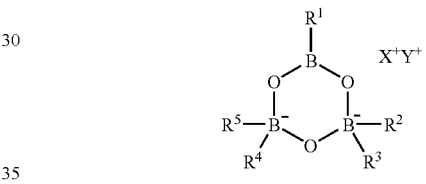

Wherein, $R_1$, $R_2$, $R_3$, $R_4$ and $R_5$ are independently OH or halogen; $X^+Y^+$ are independently from each other an univalent ion, or together a bivalent ion, in the treatment and/or prevention of benignant and malignant changes of the skin.

In the following the above compound will be generically referred to as a boroxine compound.

In the context of chemical experiments, the present inventors found by casual contacting the boroxine compound on a nevus on the skin that an essential complete removal of nevus was affected followed by a complete regeneration of the skin area. Further in vitro testing of this initial finding underlined this effect showing that these compounds are effective in the inhibition of growth/proliferation of tumor cells derived from the skin as well.

Hence the boroxine compounds detailed above are suitable for incorporation in pharmaceutical, cosmetic or dermatological formulations and capable to efficiently remove both, benignant changes of the skin, such as irregularly pigmented areas, as well as malignant changes of the skin, such as skin cancer.

In addition, the present inventors report herein for the first time of the use of the boroxine compounds in a medical field.

The boroxine compounds are highly water soluble which renders them on the one hand suitable for incorporation in conventional medical regimens and dermatological/cosmetical formulations and on the other hand provides a high bioavailability, which is underlined by a good absorption thereof into the skin area applied to, while a long term effect indicates a slow degradation of the boroxine compound. It has further been found in extensive toxical studies that the boroxine compounds have no detrimental effects on the health of humans or other mammals. In particular, no signs of irritation of the treated skin areas were visible.

The boroxine compounds and salts thereof may be prepared according to standard techniques well known to the skilled person as e.g. reported by Ryss I. G., Slutskaya M. M., Report on the Platinum Sector 26 (1951), 216 in Ryss, I. G., The Chemistry of Fluorine and its Inorganic Compounds, State Publishing House for Scientific, Technical and Chemical Literature, Moscow 1956 (English Translation U.S. Atomic Energy Commision Translation Series AEC-tr-3927.), pp. 558-560.

As indicated above, $R_1$, $R_2$, $R_3$, $R_4$ and $R_5$ are independently hydroxy (OH) or halogen, such as fluorine, chlorine, bromine and/or iodine. Preferably, the residues $R_1$, $R_2$, $R_3$, $R_4$ and $R_5$ are independently from each other OH or fluorine. More preferably, $R_1$ is fluorine and $R_2$, $R_3$, $R_4$ and $R_5$ are fluorine; still more preferably $R_1$, $R_3$, $R_4$ and $R_5$ are fluorine and $R_2$ is OH.

$X^+Y^+$ are independently from each other an univalent ion or together a bivalent ion. The term "univalent ion" is directed to metallic ions having a single positive charge with hydrogen being excluded. Bivalent ions relate to metallic ions with a double positive charge. Preferably the metallic ions are selected from among member naturally occurring in the body, examples of which, for univalent ions, are members of the first main group, such as Li, Na, K and for bivalent ions Mg and Ca. Preferably, $X^+Y^+$ are both univalent ions and more preferably $X^+Y^+$ are both K.

According to a first embodiment the compound has the structural formula $K_2[B_3O_3F_4OH]$ having $R_1$=OH and $R_2$, $R_3$, $R_4$ and $R_5$=F or $R_1$, $R_3$, $R_4$ and $R_5$=F and $R_2$=OH.

It is understood that any enantiomer of the above compound is comprised.

According to a preferred embodiment a pharmaceutical, dermatological or cosmetic composition is disclosed which comprises as an active ingredient a boroxine compound as detailed above and a pharmaceutically, cosmetically or dermatologically acceptable carrier.

This active ingredient may, where desired, be present in form of a pharmaceutically, cosmetically or dermatologically acceptable salt, which may be prepared as alkaline metal or alkaline earth salts, such as sodium, potassium or calcium salts. Organic salts and esters are also suitable for use with this invention.

According to another embodiment, the compositions of the present invention are formulated in any suitable manner for application to an individual's skin. Preferably, the composition is in a form appropriate for topical application, more preferably suitable for the application to the face, hands, bust or body, such as to the face or hands. The composition may also be used as a bust-firming composition or body-firming composition. It is preferred that said compositions are formulated as a lotion, face mask, skin patch, cream, ointment, water-based liquid, oil-based liquid, paste or sprayable liquid. More preferably, said composition is formulated as a cream or lotion. In another preferred embodiment, said composition is a face mask or skin patch. Alternatively the pharmaceutical composition is in a form rendering it suitable for subcutaneous injection directly below the skin area to be treated.

In one preferred embodiment of the present invention, said formulation may contain ingredients such as absorbent particles (e.g. polymer beads or micelles) that provide sustained release of the compounds of the present invention to the skin. In one preferred embodiment, the formulations of the compositions of the present invention are hypoallergenic, i.e. cause at the most a very low level of allergic reactions.

Compositions of the present invention can be directly applied, preferably to the skin, by any appropriate method, such as a spray bottle, a droplet bottle, a moisturized cotton ball or pad, suitable applicators such as paddles or strips, or by hands or fingers. In one preferred embodiment of the invention, compositions of the present invention may also be applied in a skin patch that incorporates cosmetic or pharmaceutical substances therein. In another, equally preferred embodiment of the present invention, compositions of the present invention may be applied in a skin "mask", preferably in the form of a gels or paste.

Another preferred form for topical delivery of the compounds of the present invention is a hot compress comprising a woven or non-woven fibrous wrap impregnated with one or more compounds of the present invention. It is preferred that prior to treatment the impregnated fibrous wrap is immersed in warm water to at least partially solubilize the active component and is wrapped around the area to be treated. Another preferred form of topical delivery is film-forming materials loaded with the compositions of the present invention. Such film-forming materials are, for example, disclosed in U.S. Pat. No. 4,623,539. Said film-forming polymers may include certain anionic, cationic and neutral polymers.

The compositions of the present invention include a cosmetically or pharmaceutically or dermatologically acceptable carrier. The total amount of the carrier preferably ranges from about 10 to about 99.9%, preferably from about 50 to about 90%, optimally from about 70 to about 85% by weight of the formulation.

The expression "cosmetic or dermatological or pharmaceutical acceptable carrier" refers to a vehicle, for either cosmetic, dermatological or pharmaceutical use, which delivers the active components to their site of action and will not cause significant harm to the human or animal recipient. Any carrier selected for use in the therapeutic and cosmetic compositions should be pharmaceutically and/or cosmetically acceptable and appropriate for the form in which the composition will be used, e.g., cream, gel, milk, oil, lotion, face mask, skin patch, ointment, water-based liquid, oil-based liquid, paste, sprayable liquid and the like. Preferably, the carrier has an affinity for the skin, and/or is well tolerated and/or stable and/or it is used in an amount adequate to provide the desired consistency and ease of application.

The physiologically acceptable carrier, in which the boroxine compound may be used, its amount, the galenic form of the composition and its preparation mode, may be selected by the skilled person on the basis of its general knowledge depending on the type of the desired composition. Those skilled in the art will appreciate that a wide variety of pharmaceutically or cosmetically-acceptable carriers may be employed according to the present invention. Examples of such carriers are described in U.S. Pat. No. 4,877,805, which is incorporate herein by way of reference.

Said carrier may be a simple combination of a buffered solution of propylene glycol, and an acrylate gelation agent, or any of a wide variety of known or commercially available formulations for e.g. creams or lotions. More than one type of carrier may be used.

For applying onto the skin, the composition can have the form in particular of an aqueous or an oily solution; of a dispersion of the lotion or serum type, of emulsions of liquid or semi-liquid consistency of the milk type obtained through dispersion of a fatty phase into an aqueous phase (O/W) or reversely (W/O); of suspensions or emulsions of a soft consistency of the cream type or aqueous or anhydrous gel type; of microcapsules or micro particles; of vesicular dispersions of the ionic and/or non ionic type. When the composition is in an aqueous form, in particular in an aqueous dispersion, emulsion or solution, it can comprise an aqueous phase, which may comprise water, flower water and/or mineral water. Said aqueous phase can additionally comprise alcohols such as Ci-Cemonoalcohols and/or polyols such as glycerol, butylenes glycol, isoprene glycol, propylene glycol, polyethylene glycol. Ointments and creams may be formulated with an aqueous or oil base with the addition of suitable thickening or gelling agents. Lotions may be formulated with an aqueous or oily base. Powders may be formulated with the aid of any suitable powder base, such as talc, lactose, starch and the like. Ointments, pastes, creams and gels of the present invention may contain excipients, such as paraffin, starch, tragacanth, cellulose derivatives, polyethylene glycols, silicones, talc and zinc oxide. Generally, the carrier can be anhydrous or aqueous. It can thus comprise an aqueous phase and/or a fatty phase.

Thus, in one preferred embodiment of the present invention, the compositions comprise a fatty phase, in particular made of fatty bodies liquid at 25 C., such as oils from animal, vegetable, mineral or synthetic origin, either volatile or not, fatty bodies solid at 25 C such as waxes from animal, vegetable, mineral or synthetic origin; of pasty fatty bodies; of gums; and the mixtures thereof. The volatile oils are generally oils having, at 25 C, a saturating vapour tension at least equal to 0.5 millibar (50 Pa). Fatty phase components include, but are not restricted to: cyclic volatile silicones having 3 to 8 silicon atoms, preferably 4 to 6, cyclo-copolymers of the dimethylsiloxane/methylalkylsiloxane type, linear volatile silicones with 2 to 9 silicon atoms, hydrocarbon volatile oils, such as isoparaffins and, more particularly, isododecane and fluorinated oils, poly(C1-C20) alkylsiloxanes and, more particularly, those with trimethylsilyl end groups, amongst which linear polydimethylsiloxanes and alkylmethylpolysiloxanes, silicones modified by aliphatic and/or aromatic groups, optionally fluorinated, or by functional groups such as hydroxyl, thiol and/or amine groups, phenylated silicone oils, oils from animal, vegetable or mineral origin, in particular animal or plants oils made of esters of fatty acids and polyols, in particular liquid triglycerids, for example sunflower, corn, soya, marrow, grape seed, sesame, hazel-nut, apricot, almond, or avocado oils; fish oils, glycerol tricaprocaprylate, or plant or animal oils having the formula R1COOR2, where R1 represents the residue of a superior fatty acid having 7 to 19 carbon atoms and R2 represents a branched hydro-carbon chain having 3 to 20 carbon atoms, for example Purcellin oil; paraffin oil, liquid paraffin, perhydrosqualene, wheat germ, calophyllum, sesame, macadamia, grape seed, colza, copra, arachis, palm, castor, jojoba, olive or cereal germ oils; fatty acid esters; alcohols; acetylglycerides; octanoates, decanoates or ricinoleates from alcohols or polyalcohols; fatty acid triglycerids; glycerols; fluorinated and per-fluorinated oils; silicone gums; waxes from animal, vegetable, mineral or synthetic origin, such as microcrystalline waxes, paraffin, petrolatum, liquid paraffin, ozokerite, Montan wax; beewax, lanolin, and the derivatives thereof; Candelilla, Ouricury and Japan waxes, cocobutter, cork fibre or sugar cane waxes; hydrogenated oils solid at 25 C, ozokerites, fatty esters and glycerides solid at 25 C; polyethylene waxes and waxes obtained through Fischer-Tropsch synthesis; hydrogenated oils solid at 25 C; lanolins; fatty esters solid at 25 C; silicone waxes and fluorinated waxes.

Other suitable carriers for use with the present invention include, but are not limited to, water, mineral oil, ethylene glycol, propylene glycol, lanolin, glyceryl stearate, sorbitan stearate, isopropyl myristate, isopropyl palmitat, acetone, glycerol, phosphatidylcholine, sodium cholate, or ethanol.

The composition according to the invention can also comprise at least one co-emulsifier, which includes, but is not restricted to, oxyethylenated sorbitan monostearate, fatty alcohols such as stearyl alcohol or cetyl alcohol, or esters of fatty acids and polyols such as glyceryl stearate.

The compositions may also be combined with a skin penetration enhancer. The enhancers, helping to transport the active components through the normal intact skin, include, but are not limited to DMSO (dimethylsulfoxide), liposomes, mixed lipid micelles, ethosomes, transfersomes, niosomes, ethanol, amides, ethers, glycols, hydrocarbon oils, sodium lauryl sulfate, oleic acid, hydroalcoholic solution, and soya phosphatidylcholine or their combinations. Other skin penetration enhancers include the use different pH values, co-solvents, surfactants, cyclodextrins, and iontophoresis. Said skin penetration enhancer is preferably in an amount ranging from 0.01 to 30% by weight based on the total weight of the composition. In one preferred embodiment, said skin penetration enhancer is a natural surfactants or an artificial surfactant such as isopropyl myristate.

Suitable solvents which can be used include lower alcohols, in particular, ethanol and isopropanol, and propylene glycol. Suitable hydrophilic gelling agents include carboxyvinyl polymers (carbomer), acrylic copolymers such as acrylate/alkylacrylate copolymers, polyacrylamides, polysaccharides such as hydroxypropylcellulose, natural gums and clays. Suitable lipophilic gelling agents include modified clays such as bentones, metal salts of fatty acids such as aluminum stearates, and hydrophobic silica, or alternatively ethylcellulose and polyethylene.

Preferably, the compositions of the present invention are stabilized. In general, stabilization methodologies and techniques that may be used in accordance with the present invention include any and all methods for the stabilization of chemical or biological material known to the art, including e.g. the addition of chemical agents, temperature modulation based methodologies; radiation based methodologies or combinations thereof. Chemical agents that may be used in accordance with the present invention include inter alia preservative agents; acids; bases; salts; anti-oxidants; viscosity modifying agents; emulsifiers; gelling agents; and mixtures thereof.

Compositions of the invention may also include viscosity modifiers, preferably in amounts from about 0.01 to about 10% by weight of the composition. Viscosity modifiers such as cetyl alcohol, glycerol, polyethylene glycol (PEG), PEG-stearate, or Keltrol may also be used to enhance the stability of the formulation. Thickeners which may enhance the stability include gelling agents such as cellulose and derivatives, Carbopol and derivatives, carob, carrageenans and derivatives, xanthene gum, sclerane gum, long chain alkanolamides, bentone and derivatives, Kaolin USP, Veegum Ultra, Green Clay, Bentonite NFBC, magnesiun aluminum silicate (Veegum@), guar gums (such as JaguarHP-120 @), xanthan gum, sodium caroxymethyl cellulose, hydroxyalkyl and alkyl celluloses, cross-linked acrylic acid polymers, and mixtures thereof. As known to the skilled person, the precise amount of thickeners can vary depending upon the consistency and thickness of the composition which is desired.

When necessary, in the cosmetic preparation preferable for the operation mode in the present invention, ingredients such as oils, surfactants, moisturizers, thickeners, sequestering agents, ultraviolet absorbents, antiseptics, anti-oxidants, fragrances, and various drugs which are generally used in cosmetic preparations may be compounded.

Oils may be material oils which are applicable to cosmetics. For example, hydrocarbons, esters, glycerides, lower alcohols, higher alcohols, polyhydric alcohols, higher fatty acids, and organopolysiloxane fluids such as liquid paraffin, squalane, vaseline, polyisobutyrene, microcrystalline wax, isopropyl myristate, myristyl octyl dodecanol, di-(2-ethylhexyl) succinate, diisooctanoic acid neopentyl glycol, glycerine monostearate, isostearic acid triglyceride, coconut-oil fatty acid triglyceride, castor oil, ethanol, octyl dodecanol, hexadecyl alcohol, cetyl alcohol, oleyl alcohol, stearyl alcohol, polyethylene glycol, lauric acid, palmitic acid, oleic acid, stearic acid, isostearic acid, lanolin, beeswax, and olive oil may be used.

The cosmetic compositions according to the invention can take the form of any suitable cosmetic product. Preferably, the compositions take the form of a care, treatment, cleaning or protection product for the face or the body skin, including the scalp, such as a day and/or night and/or hydrating care composition for the face or the body; a composition for irritated skins; a body milk, a sun protective, artificial sun tanning (self-tanning) or after-sun care composition; a sun protective cream or gel; a face skin, body or lip makeup product, such as a foundation cream, a tinted cream, a cheek or eye-lid makeup product, a free or compact powder or a lip care product.

The composition according to the invention may also be applied to any part of the human body where skin improvement benefits are desired. Preferably, compositions of the present invention are used on areas exposed to the sun, such as the hands, scalp, face, lips arms, legs. In the most preferred embodiment of the present invention, the compositions are applied to the facial area.

Other compounds suitable for use in combination with the boroxine compound in the preparation of a respective carrier include one or more of vitamin actives, including but not restricted to vitamin A and derivatives, including retinoic acid, retinyl aldehyde, retin A, retinyl palmitat, adapalene, and beta-carotene; vitamin B (panthenol, provitamin B5, panthenic acid, vitamin B complex factor); vitamin C (ascorbic acid and salts thereof) and derivatives such as ascorbyl palmitat; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitat, vitamin E linolate and vitamin E acetate; vitamin K and derivatives; vitamin Q (ubiquinone) and mixtures thereof.

The composition is administered in an amount to be effective for the intended application and the subject to be treated. To this end, the dosage of the composition and other constituents may vary depending on age, weight, and condition of the subject. In general, the active agent is preferably administered at a concentration that will afford effective results without causing any harmful or deleterious side effects, and may be administered either as a single unit dose, or if desired in convenient subunits administered at suitable times throughout the day.

According to a preferred embodiment, the boroxine compound will be contained in the composition in an amount of about 0.01 to 10 mg per single (daily) dose, based on the compound wherein $R_1$, $R_3$, $R_4$ and $R_5$ are fluorine, $R_2$ is OH and X, Y are both K, which is usually enough for removing a single nevus but may be in case of necessity repeated. These amounts per single do not lead to any side-effects. Preferably, the boroxine compound is contained in an amount of about 0.1 to 5 mg and more preferably in an amount of 0.5 to 1 mg per single (daily) dose.

The present invention also provides for a kit comprising the composition and a delivery device. The compositions may conveniently be presented in single or multiple unit dosage forms as well as in bulk, and may be prepared by any of the methods, which are well known in the art of pharmacy.

According to a preferred embodiment the present invention provides for the first time the use of the boroxine compound in medicine/a pharmaceutical field.

Preferably, the boroxine compound or a pharmaceutically acceptable salt thereof are used for the preparation of a pharmaceutical composition allowing treatment and/or inhibition of a malignant or benignant skin disorder. Skin disorders manifest preferably in convex shaped/raised changes of the skin, such as e.g. nevus. The term nevus as used herein refers to any congenital lesion of the skin or a birthmark and be in form of a pigmented or non pigmented spot on the skin which is flat or raised, hairy, smooth, or warty. It may be also in form of a circumscribed stable malformation of the skin and occasionally of the oral mucosa, which is not due to external causes and therefore presumed to be of hereditary origin. The excess (or deficiency) of tissue may involve epidermal, connective tissue, adnexal, nervous, or vascular elements; a cutaneous haematoma.

According to still another embodiment, the use of the boroxine compound or a dermatologically or cosmetically acceptable salt thereof in a dermatological or cosmetic composition for the treatment of skin disorders is provided.

The boroxine compound may be also be present in form of a pharmaceutically, cosmetically or dermatologically acceptable salt, which may be prepared as alkaline metal or alkaline earth salts, such as sodium, potassium or calcium salts. Organic salts and esters are also suitable for use with this invention.

The pharmaceutical composition may further comprise one of the above-mentioned pharmaceutically, dermatologically or cosmetically suitable carriers comprising various ingredients, which may also exert a beneficial effect supporting that of the boroxine compound and which effect is well known to the skilled person.

According to still another embodiment, the malignant skin disorder to be treated is selected from the group consisting of malignant melanoma, basilioma, spinalioma, mycosis fungoides, fibrosarcoma, carcinoma of the sebaceous or perspiratory gland, angiosarcoma, myxosarcoma, Merkel cell carcinoma and squamous cell carcinoma.

In one embodiment the benignant skin disorder to be treated is hyperkeratosis or a precursor thereof. Such precursors comprise preferably calluses and corns, warts, eczema, keratosis pilaris, lichen planus causing hyperkeratosis inside the mouth, actinic keratosis, seborrheic keratosis and ichthyoses.

The following examples illustrate the invention without limiting it thereto.

EXAMPLES

Example 1

Investigation of anti-tumor activity of the following compound

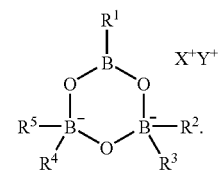

wherein $R_1$=OH and $R_2$, $R_3$, $R_4$, $R_5$=F with $X^+Y^+$=$K_2$ (termed (XS)).

An investigation of anti-tumor activity of the boroxine compound (XS) was conducted on cell lines of mouse fibro-sarcoma FsaR and mouse carcinoma SCC VII.

Cell lines (mouse fibro-sarcoma FsaR and mouse carcinoma SCC VII) were incubated at optimal conditions for 24 hours, followed by addition of tested substances in a dosage of 0.5 μg (XS100) and combinations with Li (lithium) and SNP (sodium-nitroprusside) Li (lithium) is blocker of GSK-3 (glycogen-synthetase-kinase), an enzyme involved in pathways that modulate cell's death. SNP (sodium-nitroprusside) is modulator of pro-apoptotic protein p53 (tumor suppressor protein).

Cells were additionally incubated for 24 hours in the presence of the substances. Later, cells were fixed by glutaraldehyde and stained in 0.1% crystal violet. Stain attached to the viable cells was extracted by 0.2% Triton-X 100 and extract absorbance was determined at 590 nm. Value of absorbance is proportional with viable cells number.

The following results have been obtained (the observed variation of the observed values are a maximum of 10%).

TABLE 1

Cytotoxic effect of XS, Li (lithium) and SNP (sodium-nitroprusside) substances on mouse fibro-sarcoma FsaR expressed as percentage of control (without tested substances).

| Group (substance) | % of control |
|---|---|
| Li | 100 |
| SNP | 70 |
| Li-SNP | 61 |
| XS100 | 21 |

TABLE 2

Cytotoxic effect of XS, Li (lithium) and SNP (sodium-nitroprusside) substances on mouse carcinoma cells SCC VII expressed as percentage of control (without tested substances).

| Group (substance) | % of control |
|---|---|
| Li | 97 |
| SNP | 100 |
| Li-SNP | 100 |
| XS100 | 42 |

As may be seen from the above, the present compound is much more effective as the known cytotoxic compounds Li or SNP or their combination.

Example 2

Preparation of 1 g of Adipoid Ointment

The following ointment has been prepared.

| | |
|---|---|
| 10 mg | $K_2[B_3O_3F_4OH]$ |
| 50 mg | 2-hydroxy-4-methoxybenzophenone, |
| 140 mg | macrogolstearate, |
| 140 mg | 1000-cetylstearylalcohol, |
| 140 mg | 1,2-propandiole, and |
| 520 mg | vaseline (white). |

Followed by blending to achieve a homogenous consistence.

The formulation provided to be suitable for application on the skin and penetrated well.

What is claimed is:

1. A topical pharmaceutical composition comprising:
   (a) a boroxine compound, which has the formula:

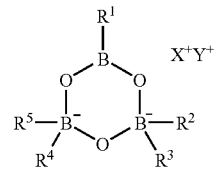

wherein
   $R_1$, $R_2$, $R_3$, $R_4$ and $R_5$ are independently from each other OH or Halogen, wherein at least one of $R_1$, $R_2$, $R_3$, $R_4$ and $R_5$ is Halogen; and
   $X^+$ and $Y^+$ are independently from each other a univalent ion or together a bivalent ion; and
   (b) a pharmaceutically, cosmetically or dermatologically acceptable carrier, wherein the composition is in the form of an ointment or cream.

2. A single dosage form of the composition according to claim 1, wherein the boroxine compound is in an amount of 0.01 to 10 mg.

3. The compound composition according to claim 1, wherein $X^+$ and $Y^+$ are independently $K^+$ and/or $Na^+$.

4. The composition of claim 1, wherein
   $R_1$ is OH;
   $R_2$, $R_3$, $R_4$ and $R_5$ are F; and
   $X^+$ and $Y^+$ are each $K^+$.

* * * * *